US00PP16759P3

(12) United States Plant Patent
Janick

(10) Patent No.: US PP16,759 P3
(45) Date of Patent: Jul. 4, 2006

(54) PEAR TREE NAMED 'H2-169'

(50) Latin Name: *Pyrus communis*
Varietal Denomination: H2-169

(75) Inventor: Jules Janick, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 130 days.

(21) Appl. No.: 10/971,719

(22) Filed: Oct. 22, 2004

(65) Prior Publication Data

US 2006/0090231 P1 Apr. 27, 2006

(51) Int. Cl.
*A01H 5/00* (2006.01)

(52) U.S. Cl. ..... Plt./176

(58) Field of Classification Search ..... Plt./176
See application file for complete search history.

(56) References Cited

U.S. PATENT DOCUMENTS

PP4,379 P * 2/1979 Janick ..... Plt./176
PP6,362 P * 11/1988 Brooks ..... Plt./179

* cited by examiner

*Primary Examiner*—Kent Bell
*Assistant Examiner*—W. C. Haas
(74) *Attorney, Agent, or Firm*—Klarquist Sparkman

(57) ABSTRACT

A new pear variety distinguished by its large size fruit of nice shape; fruit having a good quality texture and flavor; good tree type; blight tolerant (equivalent to 'Honeysweet' variety); early season (mid-August); and annual high productivity.

2 Drawing Sheets

Latin name of the genus and species of the plant claimed: *Pyrus communis.*
Variety denomination: 'H2-169'.

CROSS REFERENCE TO RELATED APPLICATIONS

None.

STATEMENT REGARDING FEDERALLY SPONSORED RESEARCH OR DEVELOPMENT

None.

BACKGROUND OF THE INVENTION

The present invention relates to a new and distinct variety of pear tree named 'H2-169'. Our new tree resulted from a planned hybridization program and is a selection from crossing 'US 571' (unpatented) as the seed parent with 'Honeysweet' (U.S. Plant Pat. No. 4,379) as the pollen parent (see FIG. 1). The resulting tree was selected when growing in a cultivated area in West Lafayette, Ind.

BRIEF SUMMARY OF THE INVENTION

The 'H2-169' variety is distinguished from other pear varieties due to the following unique combination of characteristics: large size fruit of nice shape; fruit has a good quality texture and flavor; good tree type; blight tolerant (equivalent to 'Honeysweet' variety); early season (mid-August); and annual high productivity.

Asexual reproduction of this new variety by grafting and budding onto rootstock ['Old Home×Farmingdale' variety rootstock (U.S. Plant Pat. No. 6,362)] shows that the foregoing characteristics come true to form, are firmly fixed, and are established and transmitted through succeeding propagations.

The following detailed description concerns the original tree, selected on Aug. 20, 1993, and progeny first asexually propagated in 1996. The original tree and progeny have been observed growing in a cultivated area in West Lafayette, Ind.

Certain characteristics of this variety may change with changing environmental conditions (such as photoperiod, temperature, moisture, soil conditions, nutrient availability, or other factors). For example, leaf colors may be brighter green if the trees are grown in soil with greater nitrogen concentrations, and may be more yellow when grown in soil containing lesser amounts of nitrogen. Color descriptions and other terminology are used in accordance with their ordinary dictionary descriptions, unless the context clearly indicates otherwise. Color designations (hue/value/chroma) are made with reference to The Royal Horticultural Society Colour Chart (R.H.S.).

Figure 1:
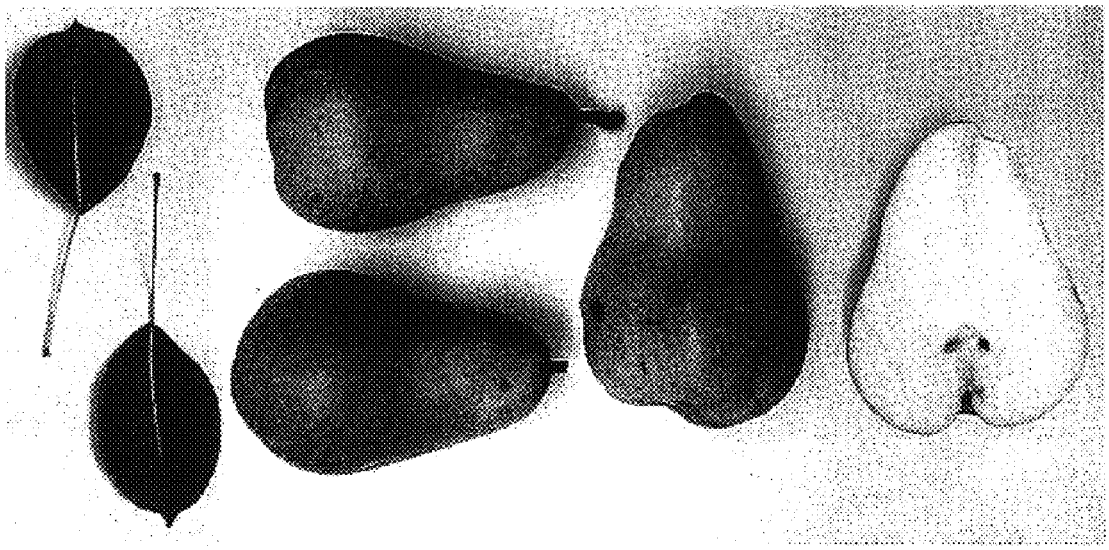
FIG. 1 is a photograph showing typical fruit and leaves of the new variety.
Figure 2:
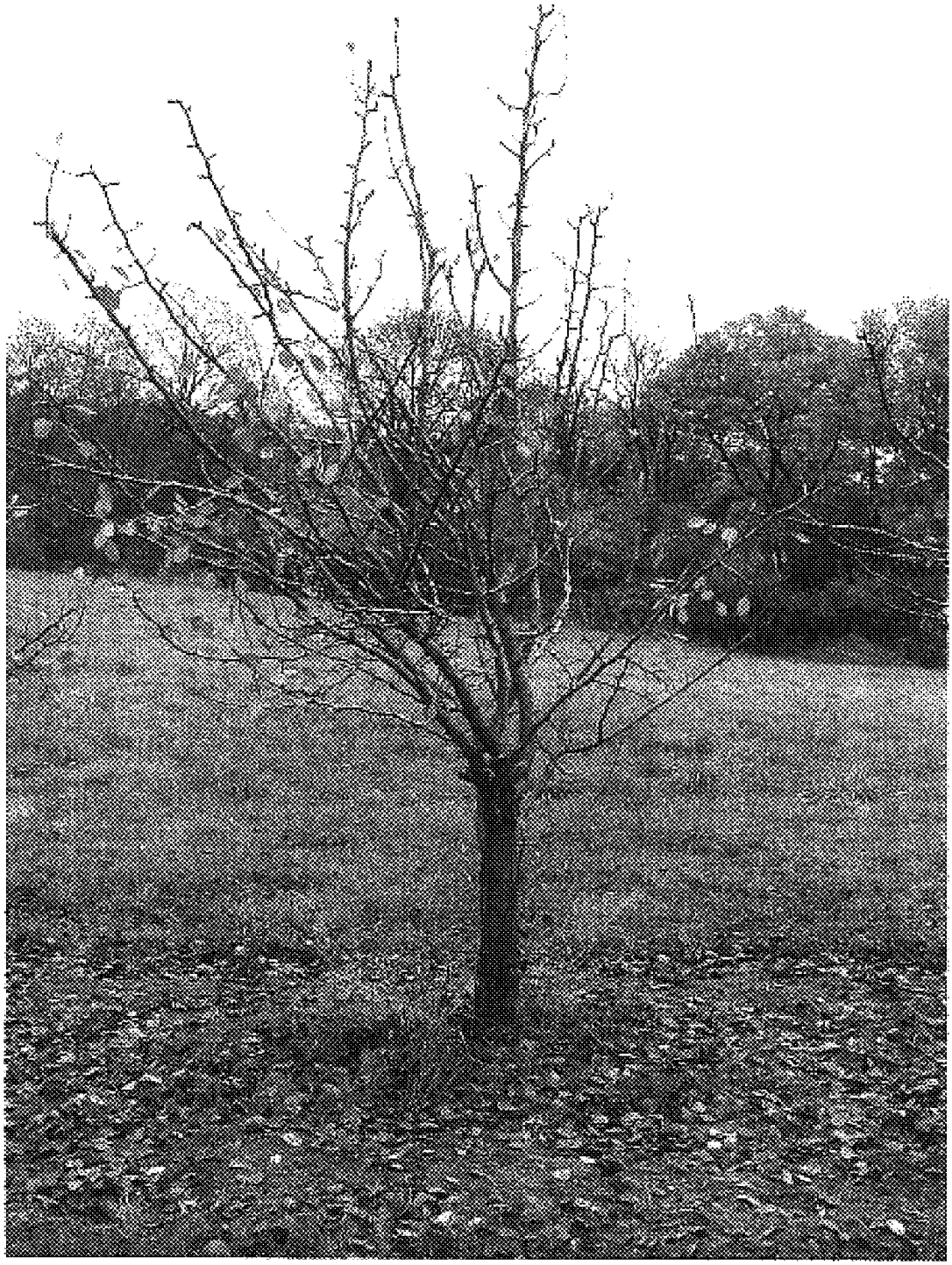
FIG. 2 is a photograph showing a tree of the new variety.

The color photographs shows typical specimens of the leaves and fruit and tree of this new pear tree variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photographs alone.

DETAILED DESCRIPTION

Botanical

The following detailed description of the 'H2-169' variety is based on observations of asexually reproduced progeny. The observed progeny are trees which were 7 years of age and growing on 'Old Home×Farmingdale' variety rootstock (U.S. Plant Pat. No. 6,362) in West Lafayette, Ind.

Scientific name: *Pyrus communis* 'H2-169'.

Parentage:

*Seed parent.*—'US 571' (unpatented), which resulted from a cross between 'Michigan US 437' (unpatented) and 'Comice' (unpatented).

*Pollen parent.*—'Honeysweet' (U.S. Plant Pat. No. 4,379).

Tree:

*Vigor.*—Vigorous.

*Overall shape.*—Rounded.

*Height.*—About 10 to 12.

*Width.*—Overall spread of about 11 feet.

*Caliper.*—92 cm at 60 cm above the ground.

*Trunk.*—Medium.

*Trunk bark texture.*—Rough and scaly.

*Trunk bark color.*—Greyed-green (RHS 197A).

*Patches or other markings.*—Exfoliates, brown (RHS 200A) in color.

*Primary branches.*—Upright.

*Angle of emergence from trunk.*—About 45 degrees. Angle does not vary from top to bottom of tree.

*Branch color.*—One-year old branches are greyed-red (RHS 178A) in color, while two-year old branches are grey-orange (RHS 177B) in color.

*Branch pubescence.*—None.

*Branch lenticels.*—Medium density, approximately 5 per square centimeter; round shape, typical examples of which measured about 1.2 mm in diameter; greyed-green (RHS 197D) in color.

*Internodes.*—Average internode length is about 3 cm on a one-year old shoot.

*Bearing.*—Annual.

*Hardiness.*—Zone 5B.

*Disease resistance.*—Tolerant to fireblight, similar to the 'Honeysweet' variety.

Leaves:

*Texture.*—Smooth.

*Sheen.*—Glossy.

*Length.*—About 68 mm to about 86 mm, averaging about 76 mm in 10 leaves.

*Width.*—About 47 mm to about 59 mm, averaging about 51.2 mm in 10 leaves.

*Thickness.*—About 0.26 mm to about 0.31 mm, averaging about 0.28 mm in 10 leaves.

*Petiole.*—About 61.2 mm long and about 1.2 mm in diameter; yellow-green in color (RHS 150B). No pubescence.

*Margin.*—Smooth.

*Tip shape.*—Acuminate.

*Stipules.*—None.

*Leaf color.*—Upper leaf surface: yellow-green (RHS 146A). Lower leaf surface: yellow-green (RHS 146D). Vein: yellow-green (RHS 150B).

*Pubescence.*—None.

The length, width, thickness and other measurements were obtained from observations of ten typical leaves in West Lafayette, Ind. on Sep. 10 or 13, 2004.

Flowers:

*Size.*—Medium size, typical flower measuring about 33 mm to 35 mm across.

*Shape.*—Radially symmetrical.

*Color.*—Unopened bud: white (RHS N155D) with pink spots (RHS 49B). Opened flower: white (RHS N155D).

*Petals.*—5 petals per flower; not touching when open; rounded in shape; about 16 mm (to slightly larger) long. White in color (RHS N155D).

*Stamen.*—Arranged in a single row. 20 stamens, each about 6 mm long and white (RHS 155D) in color.

*Anthers.*—Red-purple (RHS 58D) in color.

*Pistil.*—Stigma is about 9 mm long; rounded at top; 5 styles, fused at base, and green-yellow (RHS 1D) in color.

*Sepals.*—About 5 mm and about 3.5 mm wide (at base); reflexed shape; yellow-green (RHS 144C) in color; pubescent.

*Pollen.*—Yellow (RHS 3C) in color.

*Fragrance.*—Very slight fetid.

*Bloom season.*—In 2004 in West Lafayette, Ind., full bloom observed on April 17 for 'Bartlett' (unpatented) variety; April 18 for 'H2-169' variety; and April 19 for 'Honeysweet' variety.

Fruit: (Observations from a limited number of typical fruit in West Lafayette, Ind.).

*Size.*—Large, about 91 mm long and 74 mm wide to 120 mm long and 82 mm wide.

*Form.*—Pyriform; symmetric. Length to diameter ratio 1.35; no ribbing; no lobes at calyx end.

*Cavity.*—None.

*Basin* (*blossom end*).—About 4.5 mm deep and about 25 mm wide; no pubescence.

*Stem.*—Short and stout; about 19 mm long and 4 mm in diameter; greyed-orange (RHS 165A) in color.

*Locules.*—Small; 5 locules; closed. Seeds adhere to carpel wall.

*Skin.*—Thin with glossy finish. No tendency to become waxy or oily in storage.

*Lenticels.*—Conspicuous; small and round with russetting; grey-orange (RHS 165C); no tendency to crack with maturity.

*Color.*—General color effect: occasional slight blush. Ground color: green-yellow (RHS 1D). Overcolor: orange (RHS 26A). Russetting: Present, fine, very light to heavy.

*Fruit properties after ripening time during harvest period in West Lafayette, Ind.*—Acid content: About 0.147 g/100 ml malic acid. Firmness: About 7 kg to 10 kg for green fruit and 0.5 kg to 2.2 kg for ripe fruit. Soluble solids: About 13%–15%. Starch index: On a scale of 1 (high starch) to 5 (low starch), average about 3.5 for green fruit and 5 for ripe fruit. Flavor: Sweet; mild to rich flavor. Juiciness: Juicy. Flesh color: Yellow-white (RHS 158D). Flesh texture: Smooth and buttery. No obvious grit cells, even at stem and base. Aroma: slight.

*Core.*—Basal bundle area shape; about 22 mm long and about 40 mm wide; calyx tube closed. Core lines defined weakly.

*Seed.*—About 1 seed per cell; acuminate; about 10.3 mm long and about 5.7 mm wide; greyed-purple (RHS 187A) in color.

*Fruit production.*—First picking date in 2004 in West Lafayette, Ind. was about August 12, and last picking date was about August 20.

*Storage.*—Fruit remains very fresh at room temperature for 5 days, and can be stored up to 6 weeks in cold storage (1° C.).

*Usage.*—Dessert.

I claim:

1. A new and distinct variety of pear tree, substantially as herein shown and described.

* * * * *

UNITED STATES PATENT AND TRADEMARK OFFICE

CERTIFICATE OF CORRECTION

PATENT NO. : PP 16,759 P3
APPLICATION NO. : 10/971719
DATED : July 4, 2006
INVENTOR(S) : Jules Janick It is certified that error appears in the above-identified patent and that said Letters Patent is hereby corrected as shown below:

Column 3, line 15, "*Height.*–About 10 to 12." should be --*Height*.–About 10 to 12 feet.--.

Signed and Sealed this

Thirtieth Day of January, 2007

JON W. DUDAS
*Director of the United States Patent and Trademark Office*